United States Patent
Jungwirth et al.

(10) Patent No.: US 9,641,764 B2
(45) Date of Patent: May 2, 2017

(54) VARIABLE FOCAL LENGTH ELEMENTS FOR ADAPTIVE OPTICAL ZOOM SYSTEMS AND METHODS

(71) Applicant: Honeywell International Inc., Morristown, NJ (US)

(72) Inventors: Matthew E. L. Jungwirth, Golden Valley, MN (US); Alan Cornett, Golden Valley, MN (US); Charles Cummings, Edgewater, MD (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/637,131

(22) Filed: Mar. 3, 2015

(65) Prior Publication Data

US 2016/0261804 A1   Sep. 8, 2016

(51) Int. Cl.
| | |
|---|---|
| *H04N 5/232* | (2006.01) |
| *G02B 15/00* | (2006.01) |
| *A61B 1/04* | (2006.01) |
| *G06T 3/40* | (2006.01) |
| *G06T 5/00* | (2006.01) |
| *G02B 3/00* | (2006.01) |
| *G02B 15/04* | (2006.01) |

(52) U.S. Cl.
CPC .......... *H04N 5/23296* (2013.01); *A61B 1/04* (2013.01); *G02B 3/0081* (2013.01); *G02B 15/00* (2013.01); *G02B 15/04* (2013.01); *G06T 3/4053* (2013.01); *G06T 5/00* (2013.01); *H04N 5/23212* (2013.01); *H04N 5/23222* (2013.01)

(58) Field of Classification Search
CPC .......... H04N 5/23296; H04N 5/23222; H04N 5/23212; G06T 5/00; G06T 3/4053; A61B 1/04; G02B 3/0081; G02B 15/00
USPC ..................................... 348/240.3
See application file for complete search history.

(56) References Cited

U.S. PATENT DOCUMENTS

| | | | | |
|---|---|---|---|---|
| 6,806,988 B2* | 10/2004 | Onuki | ...................... | G02B 3/14 359/245 |
| 2006/0067663 A1* | 3/2006 | Kita | ......................... | G02B 3/14 396/72 |
| 2008/0231966 A1* | 9/2008 | Hendriks | ................. | G02B 3/14 359/666 |
| 2012/0257085 A1* | 10/2012 | Matsumoto | .......... | H04N 1/3876 348/239 |
| 2015/0036224 A1 | 2/2015 | Jungwirth et al. | | |

OTHER PUBLICATIONS

Extended Search Report from related European Patent Application No. 16156383.8, dated Jul. 25, 2016, 5 pp.

* cited by examiner

*Primary Examiner* — Nhan T Tran
*Assistant Examiner* — Chan Nguyen
(74) *Attorney, Agent, or Firm* — Brooks, Cameron & Huebsch, PLLC

(57) ABSTRACT

Adaptive optical zoom systems and methods are described herein. One example of a system for adaptive optical zoom includes a number of variable focal length elements aligned to receive an image through an aperture, wherein the aperture is smaller than at least one of the number of variable focal length elements, a focal plane array aligned to receive the image, and a computing device coupled to the number of variable focal length elements.

19 Claims, 4 Drawing Sheets

VARIABLE FOCAL LENGTH ELEMENTS FOR ADAPTIVE OPTICAL ZOOM SYSTEMS AND METHODS

TECHNICAL FIELD

The present disclosure relates to adaptive optical zoom systems and methods.

BACKGROUND

A zoom lens is an optical imaging system that changes its magnification or focal length while keeping the relative location of the image plane stationary. A mechanical zoom lens can have a number of optical elements (e.g., lenses) and use cams or gears to adjust the spacing between the number of elements to vary the optical magnification. Adjusting the spacing between the number of elements can require submillimeter precision that has the potential of malfunctioning.

DETAILED DESCRIPTION

An adaptive optical zoom system can include a number of variable focal length elements aligned to receive an image through an aperture, wherein the aperture is smaller than at least one of the number of variable focal length elements, a focal plane array aligned to receive the image, and a computing device coupled to the number of variable focal length elements.

The adaptive optical zoom system can combine an optical zoom system coupled to an image recognition system (e.g., computing device utilizing a number of modules, microcontroller, etc.). The optical zoom system can include a number of variable focal length elements (e.g., plurality, two or more, etc.) that are aligned to focus an image on a focal plane array through an aperture. As used herein, an aperture can include an opening in a device where the opening is smaller than at least one of the number of variable focal length elements. In some embodiments, the aperture can be utilized to couple an optical device (e.g., optical scope, snake, fiber scope, etc.) to the adaptive optical zoom system. For example, the aperture can include a coupler that can be utilized to couple the adaptive optical zoom system to an optical scope.

A distance of an object from the focal plane array can be determined utilizing the image recognition system. In some embodiments, the distance of the object from the focal plane array can be determined by a distance of an optical device coupled to an aperture of the system. The distance can be utilized to determine a focal length of each of the number of variable focal length elements. The focal length of each of the number of variable focal length elements can be altered by applying and/or altering an amperage or voltage for each of the number of variable focal length elements.

The amperage or voltage provided to each of the number of variable focal length elements can be determined by the image recognition system. For example, the amperage or voltage for each of the number of variable focal length elements can be based on the determined distance and/or on a quality of the image received. The amperage or voltage for each of the number of variable focal length elements can be altered (e.g., increased, decreased, etc.) until the image received is at an optimal resolution (e.g., optimal image quality, greatest clarity compared to other amperage or voltage settings, etc.).

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of variable focal length elements" can refer to one or more variable focal length elements.

Figure 1:
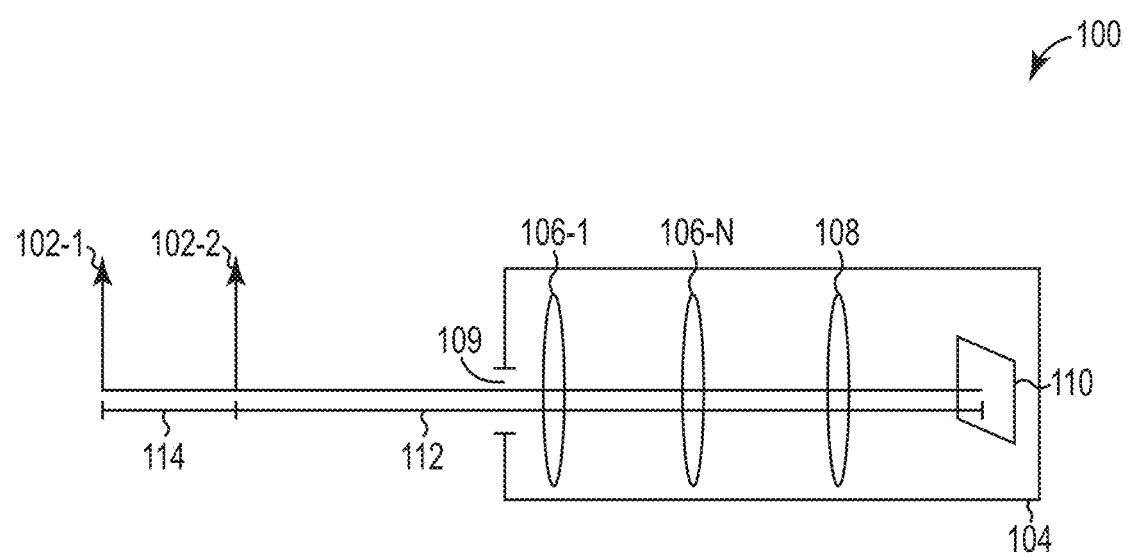
FIG. 1 illustrates an example of an adaptive optical zoom system in accordance with one or more embodiments of the present disclosure.

FIG. 1 illustrates an example of an adaptive optical zoom system 100 in accordance with one or more embodiments of the present disclosure. The optical zoom system 100 can include a number of elements: a device 104, a number of variable focal length elements 106-1, 106-N, a static focal length element 108 (e.g., singlet lens, doublet lens, etc.), an aperture 109, and/or a focal plane array 110, among other elements. The optical zoom system 100 can include a greater or fewer number of elements as shown in FIG. 1. For example, there can be a greater number of variable focal length elements 106-1, 106-N (e.g., 3 variable focal length elements, 5 variable focal length elements, N variable focal length elements, etc.). In another example, there can be a greater number of static focal length elements 108 (e.g., two static focal length elements, three static focal length elements, etc.). Increasing the number of lenses can increase the zoom capabilities (e.g., distance of objects the optical zoom system 100 can receive, type of optical device that can be coupled to the aperture 109, etc.) of the optical zoom system 100.

The device 104 can be an element (e.g., lens case, zoom element, etc.) to encase (e.g., attach, keep in a fixed position, etc.) the number of variable focal length elements 106-1, 106-N, the static focal length element 108, and/or the focal plane array 110. The device 104 can include an aperture 109 that can be smaller than the number of variable focal length elements 106-1, 106-N and/or the static focal length element 108. The device 104 can encase the number of variable focal length elements 106-1, 106-N in a fixed position relative to the focal plane array 110. For example, the device 104 can attach to the number of variable focal length elements 106-1, 106-N to prevent movement of the number of variable focal length elements 106-1, 106-N.

A distance between each of the number of variable focal length elements 106-1, 106-N and a distance from each of the number of variable focal length elements 106-1, 106-N and the focal plane array 110 can be determined (e.g., calculated, predetermined) based on a particular application (e.g., distance of objects from the focal plane array 110, desired image qualities, etc.). For example, a distance between a variable focal length element 106-1 and a variable focal length element 106-N can be determined for a desired zoom capability. In addition, a distance between the variable length element 106-1 and the focal plane array 110 can be determined for a desired zoom capability. The determined distances and/or element focal lengths can be used to estimate an aspect ratio (e.g., ratio of width and height of an image) of an image at a particular distance from the focal plane array 110.

The device 104 can encase the static focal length element 108 in a position relative to the focal plane array 110. For example, the device 104 can encase the static focal length element 108 in a fixed position that is at a particular distance from the focal plane array 110 and at a particular distance from the number of variable focal length elements 106-1, 106-N. It can be beneficial to have the static focal length element 108 relatively close to the focal plane array 110. For example, the static focal plane array 108 can be closer to the focal plane array 110 compared to the number of variable focal length elements 106-1, 106-N.

The static focal length element 108 can be attached to one or more of the number of variable focal length elements 106-1, 106-N. The static focal length element 108 attached to a variable focal length element 106-1, 106-N can produce a core element (e.g., lens core, etc.) The core element can be positioned between the number of variable focal length elements 106-1, 106-N and the focal plane array 110. The static focal length element 108 can be attached to a variable focal length element 106-N in a position that is closer to the focal plane array than the variable focal length element 106-N.

The device 104 can be used to zoom, focus, and/or increase an image quality (e.g., image size, number of identifiable pixels, amount of image distortion or artifacts, etc.) of a number of objects 102-1, 102-2 through the aperture 109. The image quality can be based on a number of image quality factors (e.g., size, sharpness, noise, dynamic range, tone reproduction, contrast, accuracy, distortion, etc.). Increasing the image quality can include altering the number of image quality factors to reduce qualities that are not desired and/or increase qualities that are desired. For example, increasing the qualities that are desired can include increasing the size of the object by zooming in on an object in order to reveal details of the object (e.g., details of a bar code, etc.). In another example, increasing the qualities can include increasing the sharpness of the image and decreasing the noise of the image. Furthermore, increasing the qualities that are desired can include increasing the size of the object through an optical device (e.g., optical scope, snake, fiber scope, etc.) that is coupled to the aperture 109.

Each of the number of objects 102-1, 102-2 can be at a distance from the focal plane array 110 (e.g., distance 112, distance 114, etc.). FIG. 1 illustrates two objects 102-1, 102-2, however embodiments are not limited to two objects. That is, there can be a greater number of objects 102-1, 102-2 than two objects. An image of one of the number of objects can be received by each of the number of variable focal length elements 106-1, 106-N, received by the static focal length element 108, and/or received by the focal plane array 110. That is, each of the number of variable focal length elements 106-1, 106-N and the static focal length element 108 can be used to focus an image of the number of objects 102-1, 102-2 on a portion of the focal plane array 110. In some embodiments, the image of one of the number of objects can be received through an aperture 109.

As described herein, the aperture 109 can be utilized to couple an optical device to the device 104. The optical device can be coupled to the device 104 to position an end of the optical device at a position that is directed towards the number of objects 102-1, 102-2. In some embodiments, the optical device can be utilized to view the number of objects 102-1, 102-2 at a position that is not accessible by the device 104. For example, the optical device can be a fiberscope that can be inserted into a human body to view objects within the body without having to create an incision that is large enough for the device 104 alone to view.

In some embodiments, the aperture 109 can be smaller than the number of variable focal length elements 106-1, 106-N, the static focal length element 108, and/or the focal plane array 110. That is, only a portion of light is received through the aperture 109 and a portion of the light is blocked by the device 104.

A focal length of each of the number of variable focal length elements 106-1, 106-N can be altered to increase an image quality of a particular object (e.g., object 102-1, object 102-2, bar code, etc.). For example, the device 104 can be directed towards object 102-2 and the focal length of the variable focal length element 106-1 and/or the focal length of the variable focal length element 106-N can be altered to increase the image quality of the object 102-2. In this example, the focal length can be altered by increasing or decreasing an amperage or voltage provided to the variable focal length element 106-1 and/or the variable focal length element 106-N.

Figure 4:
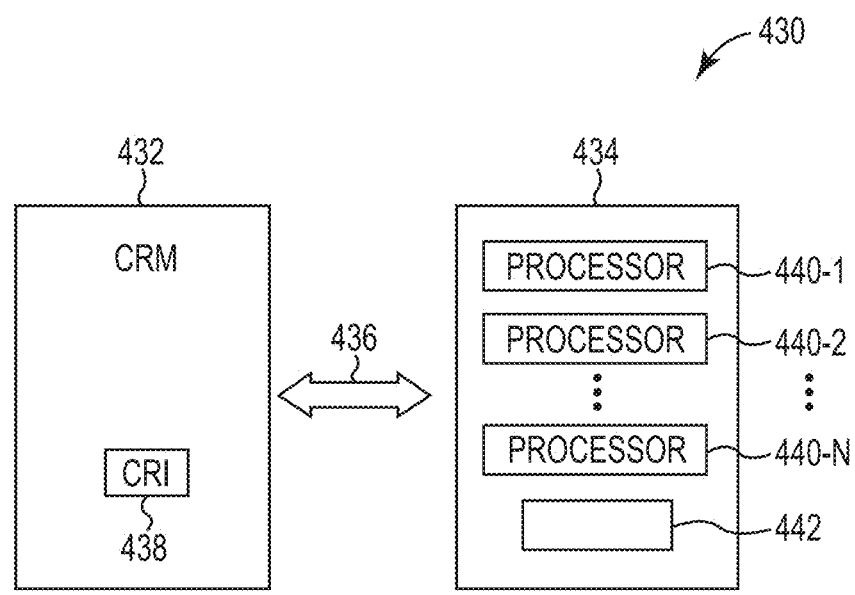
FIG. 4 illustrates a block diagram of an example of a computing device in accordance with one or more embodiments of the present disclosure.

The amperage or voltage can be increased and/or decreased by a computing device (e.g., computing device 430 as referenced in FIG. 4, amperage provider, voltage provider, etc.). The computing device can include a microcontroller that can provide specific amperage or voltage to each of the number of variable focal length elements 106-1, 106-N. Providing the amperage or voltage to each of the number of variable focal length elements 106-1, 106-N can alter the focal length of each of the number of variable focal length elements 106-1, 106-N to a desired focal length. The desired focal length can display an optimized image of an object (e.g., object 102-1, object 102-2, etc.) on the focal plane array 110.

The optimized image can include an image with a number of image qualities that are higher than other images displayed using different focal lengths for the variable focal length elements 106-1, 106-N. For example, the variable focal length element 106-1 can have a first focal length with a corresponding image quality of object 102-2. In this example, the variable focal length element 106-1 can be provided with an amperage or voltage to alter the focal length to a second focal length with a higher corresponding image quality of object 102-2. In this example, the optimized image can be the image provided when the variable focal length element 106-1 has the second focal length.

The computing device can utilize a number of resolution enhancing techniques (e.g., blind deconvolution of successive images, classical super resolution, example based super resolution, etc.). The computing device can alter the amperage or voltage of the number of variable focal length elements 106-1, 106-N based on the image qualities of the received image. For example, an image of object 102-2 can be received at the focal plane array 110 and the image qualities of the received image can be determined by the computing device. Based on the determined image qualities the computing device can alter the focal length of one or more of the variable focal length elements 106-1, 106-N and determine image qualities of the received images for each amperage or voltage alteration. The computing device can determine an optimized image based on the image qualities for the received images for each of the amperage or voltage alterations.

The computing device can alter the amperage or voltage of the number of variable focal length elements 106-1, 106-N based on a distance 112 (e.g., distance between the focal plane array 110 and object 102-2). For example, if an image of object 102-2 is a desired object (e.g., object that a user wants to receive as a focused image, etc.), a distance 112 can be determined and the computing device can alter the amperage or voltage of the number of variable focal length elements 106-1, 106-N to focus on object 102-2. In this example, amperage or voltage alterations for objects at a particular distance can be determined (e.g., predetermined) and the amperage or voltage alterations for each of the number of focal length elements 106-1, 106-N can be made based on the determined distance.

The desired image of an object (e.g., object 102-1, object 102-2, etc.) can be changed to a different image of a different object. The distance of the different image of the different object can be determined and the focal length of the number of variable focal length elements 106-1, 106-N can be altered by altering the amperage or voltage of two or more of the number of variable focal length elements 106-1, 106-N. The amperage or voltage can be altered based on the distance of the different object. For example, the desired object can change from object 102-2 to object 102-1. In this example, the determined distance can be distance 114 and the amperage or voltage of the variable focal length elements can be altered based on distance 114 to focus an image of object 102-1 on the focal plane array 110.

The distance (e.g., distance 114, distance 112, etc.) of object 102-2 can be determined by a number of methods (e.g., predetermined, calculated, device, etc.). The distance can be calculated utilizing a device and/or method connected to the device 104. For example, the distance can be determined utilizing a laser distance meter (e.g., laser distance measurer, etc.). The calculated distance can be input into the computing device in order to determine amperage or voltage alterations of the number of variable focal length elements 106-1, 106-N. The distance can also be a known distance and/or a determined (e.g., predetermined distance). The known distance can be input into the computing device in order to determine amperage or voltage alterations of the number of variable focal length elements 106-1, 106-N.

In some embodiments, the distance (e.g., distance 114, distance 112, etc.) of the number of objects 102-1, 102-2 can be determined in part by a distance of an optical device (e.g., distance of a fiber scope, distance of an end of a fiber scope in relation to the number of objects 102-1, 102-2. For example, the distance can include the distance of the optical device coupled to the aperture 109 and also include a determined distance from an end of the optical device to the number of objects 102-1, 102-2.

The adaptive optical zoom system 100 can be utilized to focus and increase the image quality of objects at a number of different distances. Altering an amperage or voltage provided to the number of variable focal length elements 106-1, 106-N to focus an image of an object can be advantageous over previous mechanical zoom systems. For example, by altering the focal length of the variable focal length elements 106-1, 106-2 in a fixed position it eliminates the need of precise mechanics to change the position of the lenses. In particular environments it can be beneficial to have a device that is capable of providing an image with an increased size and/or image qualities without relying on moving parts that if altered by the environment could increase the chance of malfunction. In addition, by utilizing the variable focal length elements 106-1, 106-N in a fixed position the total mass of the adaptive optical zoom system 100 can be relatively low compared to systems utilizing mechanical zoom.

Furthermore, the adaptive optical zoom system 100 can be a mobile device that is capable of being utilized as a field tool without utilizing mechanical zoom which could malfunction under exterior conditions. For example, mechanical zoom could be damaged by dust and/or debris from exterior conditions and not function properly. In addition, the adaptive optical zoom can be relatively resistant to physical damage compared to mechanical zoom devices. For example, mechanical zoom systems can be easily misaligned from being dropped or bumped into another object. In contrast, the adaptive optical zoom system 100 does not rely on mechanical movement of lenses that can be misaligned by physical interactions. Thus, the adaptive optical zoom system 100 can be coupled to an optical device via the aperture 109 and be utilized in various exterior environments that may have elements (e.g., dirt, sand, harsh weather, etc.) that could lead to a mechanical zoom device to be damaged or malfunction.

Figure 2:
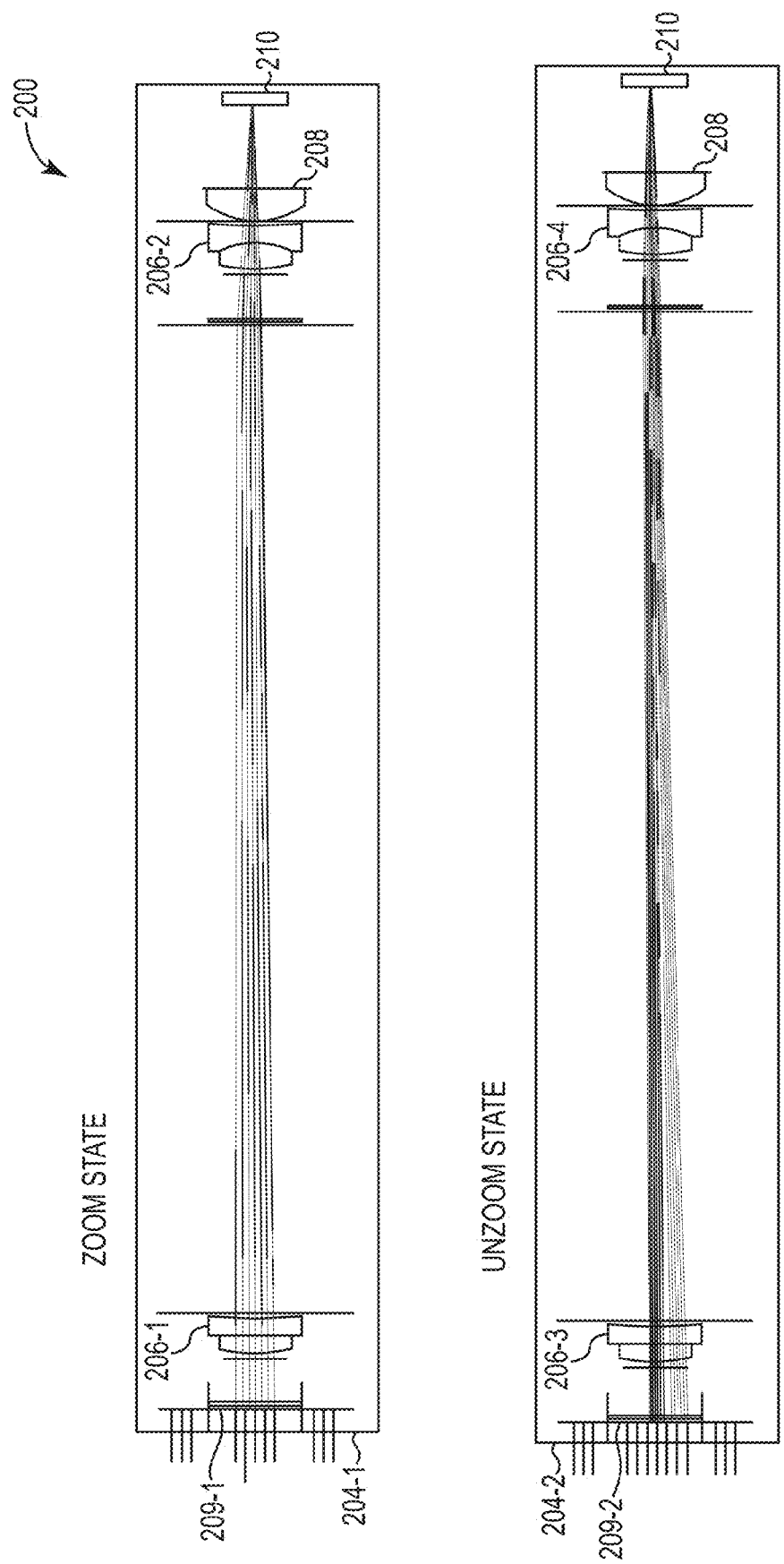
FIG. 2 illustrates an example of an adaptive optical zoom system in accordance with one or more embodiments of the present disclosure.

FIG. 2 illustrates an example of an adaptive optical zoom system 200 in accordance with one or more embodiments of the present disclosure. The adaptive optical zoom system 200 can include a device 204-1 that represents a zoom state and device 204-2 that represents an unzoom state. Device 204-1 can be the same as device 204-2 with a different amperage or voltage applied to a number of the variable focal length elements 206-1, 206-2, 206-3, 206-4.

The device 204-1 in a zoom state can include a number of variable focal length elements (e.g., variable focal length element 206-1, variable focal length element 206-2, etc.). As described herein, the number of variable focal length elements 206-1, 206-2 can be polymer lenses (e.g., Optotune EL-6-18, etc.). The device 204-1 can include a variable focal length element 206-2 that is attached to a static focal length element 208. Attaching a variable focal length element 206-2 to a static focal length element 208 can create a core element (e.g., lens core, etc.).

The number of variable focal length elements 206-1, 206-2, the static focal length element 208, and a focal plane array 210-1 can be in a fixed position within the device (e.g., device 204-1, device 204-2, etc.). For example, the number of variable focal length elements 206-1, 206-2, the static focal length element 208, and a focal plane array 210-1 can be attached to the interior of the device 204-1. The variable focal length element 206-1 in a zoom state represented by device 204-1 can be in the same location as variable focal length element 206-3 represented in an unzoom state by device 204-2. That is, the focal length of variable focal length element 206-1 can change to the focal length of variable focal length element 206-3 without changing position relative to the focal plane array or relative to the other focal length elements (e.g., variable focal length elements 206-2, 206-4, static focal length element 208, etc.) within the device (e.g., device 204-1, device 204-2).

The number of variable focal length elements 206-1, 206-2 can receive a first amperage or voltage from a computing device that produces a first focal length. The first amperage or voltage can produce a focal length that represents a zoom state. For example, the device 204-1 can represent a variable focal length element 206-1 with a particular focal length for the variable focal length element 206-1 that results in a zoom state (e.g., providing an image of an object with an increased size over an unzoom state). The amperage or voltage provided to the number of variable focal length elements 206-1, 206-2 can be altered to alter the focal length of the number of variable focal length elements 206-1, 206-2. For example, the amperage of the variable focal length element 206-1 can be altered from a first amperage or voltage and first corresponding focal length to a second amperage or voltage and second corresponding focal length.

The second amperage or voltage and second corresponding focal lengths can be represented in device 204-2. The second amperage or voltage and second corresponding focal length for the variable focal length element 206-1 and variable focal length element 206-2 can be represented by the variable focal length elements 206-3 and variable focal length element 206-4 respectively. Altering the focal length of the number of variable focal length elements from a zoom state to an unzoom state can alter (e.g., increase, decrease) a size and/or image qualities of an image displayed on the focal plane array (e.g., focal plane array 210-1, focal plane array 210-2, etc.).

Figure 3:
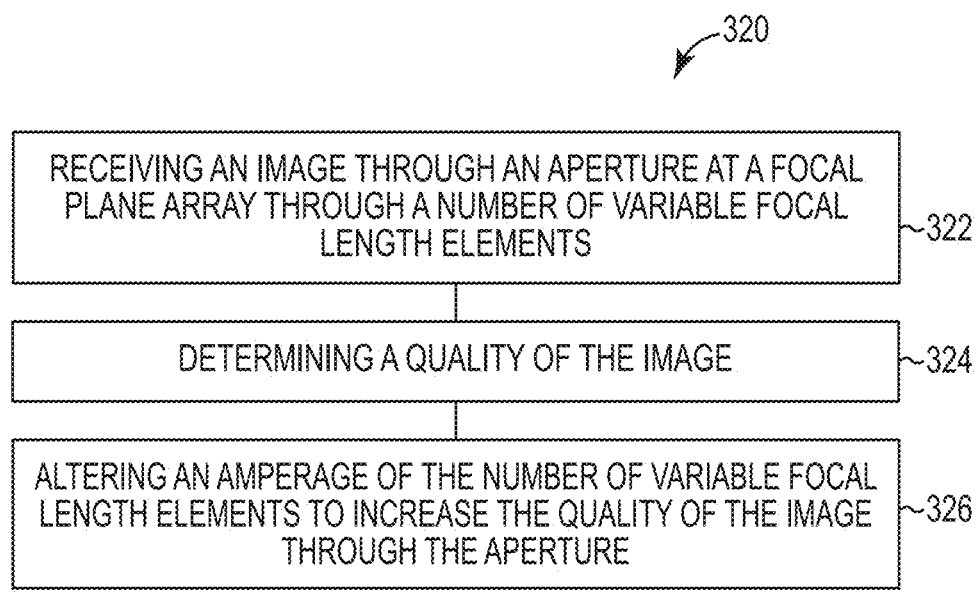
FIG. 3 illustrates an example method for an adaptive optical zoom in accordance with one or more embodiments of the present disclosure.

FIG. 3 illustrates an example method 320 for an adaptive optical zoom in accordance with one or more embodiments of the present disclosure. The method 320 can be utilized to increase a number of image qualities and/or size of an image using an adaptive optical zoom. The method can be performed utilizing a device (e.g., device 104 as referenced in FIG. 1, device 204-1 and device 204-2 as referenced in FIG. 2, etc.).

At 322 the method 320 can include receiving an image through an aperture at a focal plane array through a number of variable focal length elements. Receiving the image at a focal plane array can include utilizing a device with a number of variable focal length elements in a fixed position. For example, the number of variable focal length elements can be fixed at a position to focus an image of an object on the focal plane array.

Receiving the image at the focal plane can include directing a device at an object to focus an image of the object on the focal plane array. An image of the object can be focused and/or altered by the number of variable focal length elements to be displayed on the focal plane array.

At 324 the method 320 can include determining a quality of the image. Determining the quality of the image that is received at the focal plane array can include evaluating a number of image quality factors (e.g., size, sharpness, noise, dynamic range, tone reproduction, contrast, accuracy, distortion, etc.) of the received image.

The quality of the image can be used to determine an optimal focal length for the number of variable focal length elements. For example, a computing device (e.g., computing device 430 as referenced in FIG. 4, etc.) can utilize the quality of the received image and determine if the number of variable focal length elements should be altered to increase the quality of the received image. The computing device can utilize a plurality of received images to determine an optimal focal length for the number of variable focal length elements. For example, the computing device can determine an image quality for multiple images of an object where each of the variable focal length elements includes a different focal length. In this example, the optimal focal length can be determined by evaluating and comparing the image quality of the multiple images of the object and determining an image with a desired image quality (e.g., largest image, sharpest image, etc.).

At 326 the method 320 can include altering an amperage or voltage of the number of variable focal length elements to increase the quality of the image through the aperture. Altering the amperage or voltage of the number of focal length elements can include utilizing a computing device to provide a different amperage or voltage to a single and/or multiple variable focal length elements. As described herein, providing a particular amperage or voltage to a variable focal length element can provide a particular focal length for the variable focal length element. Altering the focal length of the number of focal length elements can alter the quality of the image. For example, altering the focal length of the variable focal length elements can increase the size of the received image on the focal plane array.

The method 320 can include also determining a distance of an object from the focal plane array. As described herein, determining a distance of an object can include utilizing a number of devices to determine the distance between the object and the focal plane array. The distance of the object from the focal plane array can be used to determine alterations for the focal length of the variable focal length elements. For example, it can be determined that when focusing on an object at a particular distance that the focal length of the variable focal length elements should be altered to a predetermined setting corresponding to the particular distance. In this example, the amperage or voltage can be altered for the number of variable focal length elements to alter the focal lengths to the predetermined settings based on the determined distance.

FIG. 4 illustrates a block diagram of an example of a computing device 430 in accordance with one or more embodiments of the present disclosure. The computing device 430 can include a communication interface (e.g., wireless network interface controller, IEEE 802.11 adapters, etc.) for receiving wireless data. The communication interface can be integrated in the computing device 430 and/or be an external card.

The computing device 430, as described herein, can also include a computer readable medium (CRM) 432 in communication with processing resources 440-1, 440-2, ..., 440-N. CRM 432 can be in communication with a device 434 (e.g., a Java® application server, among others) having processor resources 440-1, 440-2, ..., 440-N. The device 434 can be in communication with a tangible non-transitory CRM 432 storing a set of computer-readable instructions (CRI) 438 (e.g., modules) executable by one or more of the processor resources 440-1, 440-2, ..., 440-N, as described herein. The CRI 438 can also be stored in remote memory managed by a server and represent an installation package that can be downloaded, installed, and executed. The device 434 can include memory resources 442, and the processor resources 440-1, 440-2, ..., 440-N can be coupled to the memory resources 442.

Processor resources 440-1, 440-2, ..., 440-N can execute CRI 438 that can be stored on an internal or external non-transitory CRM 432. The processor resources 440-1, 440-2, ..., 440-N can execute CRI 438 to perform various functions. For example, the processor resources 440-1, 440-2, ..., 440-N can execute CRI 438 to perform a number of functions (e.g., determining a quality of an image, altering an amperage or voltage of the number of variable focal length elements, determining a distance of an object from the focal plane array, etc.). A non-transitory CRM (e.g., CRM 432), as used herein, can include volatile and/or non-volatile memory. Volatile memory can include memory that depends upon power to store information, such as various types of dynamic random access memory (DRAM), among others. Non-volatile memory can include memory that does not depend upon power to store information. Examples of non-volatile memory can include solid state media such as flash memory, electrically erasable programmable read-only memory (EEPROM), phase change random access memory (PCRAM), magnetic memory such as a hard disk, tape drives, floppy disk, and/or tape memory, optical discs, digital versatile discs (DVD), Blu-ray discs (BD), compact discs (CD), and/or a solid state drive (SSD), as well as other types of computer-readable media.

The non-transitory CRM 432 can also include distributed storage media. For example, the CRM 432 can be distributed among various locations.

The non-transitory CRM 432 can be integral, or communicatively coupled, to a computing device, in a wired and/or a wireless manner. For example, the non-transitory CRM 432 can be an internal memory, a portable memory, a portable disk, or a memory associated with another computing resource (e.g., enabling CRIs to be transferred and/or executed across a network such as the Internet).

The CRM 432 can be in communication with the processor resources 440-1, 440-2, ..., 440-N via a communication path 436. The communication path 436 can be local or remote to a machine (e.g., a computer) associated with the processor resources 440-1, 440-2, ..., 440-N. Examples of a local communication path 436 can include an electrical bus internal to a machine (e.g., a computer) where the CRM 432 is one of volatile, non-volatile, fixed, and/or removable storage medium in communication with the processor resources 440-1, 440-2, ..., 440-N via the electrical bus. Examples of such electrical buses can include Industry Standard Architecture (ISA), Peripheral Component Interconnect (PCI), Advanced Technology Attachment (ATA), Small Computer System Interface (SCSI), Universal Serial Bus (USB), among other types of electrical buses and variants thereof.

The communication path 436 can be such that the CRM 432 is remote from the processor resources e.g., 440-1, 440-2, ..., 440-N, such as in a network relationship between the CRM 432 and the processor resources (e.g., 440-1, 440-2, ..., 440-N). That is, the communication path 436 can be a network relationship. Examples of such a network relationship can include a local area network (LAN), wide area network (WAN), personal area network (PAN), and the Internet, among others. In such examples, the CRM 432 can be associated with a first computing device and the processor resources 440-1, 440-2, ..., 440-N can be associated with a second computing device (e.g., a Java® server).

As described herein, a "module" can include computer readable instructions (e.g., CRI 438) that can be executed by a processor to perform a particular function. A module can also include hardware, firmware, and/or logic that can perform a particular function.

As used herein, "logic" is an alternative or additional processing resource to execute the actions and/or functions, described herein, which includes hardware (e.g., various forms of transistor logic, application specific integrated circuits (ASICs)), as opposed to computer executable instructions (e.g., software, firmware) stored in memory and executable by a processor.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above elements and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system, comprising:
a number of variable focal length elements aligned to receive an image of an object through an aperture that is coupled to an optical device with a distance from the number of variable focal length elements, wherein the aperture is smaller than at least one of the number of variable focal length elements;
a focal plane array aligned to receive the image through the aperture and the number of variable focal length elements; and
a computing device coupled to the number of variable focal length elements to:
determine a distance between the number of variable focal length elements and a distance between the number of variable focal length elements and the focal plane array;
estimate a ratio of width and height of the image of the object at a particular distance from the focal plane array based on the distance between the number of variable focal length elements and the focal plane array;
compare image quality factors of the image to image quality factors of a plurality of other images of the object captured by the focal plane array, wherein the image quality factors include at least one of sharpness, noise and dynamic range;
determine a focal length and corresponding amperage for each of the number of variable focal length elements;
determine an optimal focal length and corresponding amperage for each of the number of variable focal length elements to increase the image quality factors for the object based on the comparison of image quality factors; and
provide the corresponding amperage to each of the number of variable focal length elements, wherein each of the number of variable focal length elements includes a different focal length.

2. The system of claim 1, comprising a number of static focal length elements.

3. The system of claim 2, wherein the number of static focal length elements are attached to at least one of the number of variable focal length elements.

4. The system of claim 1, wherein the number of variable focal length elements include a polymer variable focal length lens.

5. The system of claim 1, wherein each of the number of variable focal length elements receive an amperage or voltage of energy from the computing device.

6. The system of claim 5, wherein the focal length of each of the number of variable focal length elements is based on the received amperage or voltage of energy.

7. The system of claim 1, wherein the number of variable focal length elements are in a fixed position.

8. A method for adaptive optical zoom, comprising:
receiving an image through an aperture that is coupled to an optical device with a distance at a focal plane array through a number of variable focal length elements;
determining a distance between the number of variable focal length elements and the focal plane array;
estimating a ratio of width and height of the image of the object at a particular distance from the focal plane array based on the distance between the number of variable focal length elements;
comparing image quality factors of the image to image quality factors of a plurality of other images of the object captured by the focal plane array, wherein the image quality factors include at least one of sharpness, noise and dynamic range;
determining a focal length and corresponding amperage for each of the number of variable focal length elements;
determining an optimal focal length and corresponding amperage for each of the number of variable focal length elements to increase the image quality factors for the object based on the comparison of image quality factors; and
altering the amperage or voltage of the number of variable focal length elements to increase the quality of the image through the aperture.

9. The method of claim 8, wherein receiving the image through the aperture includes receiving the image through a catheter.

10. The method of claim 8 wherein altering the amperage or voltage of the number of variable focal length elements includes focusing the number of variable focal length elements through a center of the aperture.

11. The method of claim 8, wherein altering the amperage or voltage includes reducing image imperfections by utilizing a resolution enhancing technique.

12. The method of claim 8, wherein altering the amperage or voltage includes implementing a number of post processing techniques to increase the quality of the image.

13. The method of claim 8, wherein altering the amperage or voltage includes estimating an aspect ratio of the image based on a number of known features of the image.

14. A system, comprising:
a number of variable focal length elements aligned to focus an image of an object on a focal plane array;
a casing encompassing the number of variable focal length elements, wherein the casing comprises an aperture that is smaller than at least one of the number of variable focal length elements, wherein the aperture is coupled to an optical device that comprises a distance; and
a computing device coupled to each of the number of variable focal length elements and to the focal plane array, wherein the computing device includes instructions to:
determine a distance between the number of variable focal length elements and a distance between the number of variable focal length elements and the focal plane array;
estimate a ratio of width and height of the image of the object at a particular distance from the focal plane array based on the distance between the number of variable focal length elements and the focal plane array;
determine a quality of the image received at the focal plane array;
determine the distance of the optical device;
compare image quality factors of the image to image quality factors of a plurality of other images of the object captured by the focal plane array, wherein the image quality factors include at least one of sharpness, noise and dynamic range;
determine a focal length and corresponding amperage for each of the number of variable focal length elements;
determine an optimal focal length and corresponding amperage for each of the number of variable focal length elements to increase the image quality factors for the object based on the comparison of image quality factors; and
alter an amperage or voltage of the number of variable focal length elements based on the determined distance and the optimal focal length to increase the quality of the image, wherein each of the number of variable focal length elements includes a different focal length.

15. The system of claim 14, comprising a static focal length element between the number of variable focal length elements and the focal plane array.

16. The system of claim 14, wherein the computing device is a microcontroller.

17. The system of claim 14, wherein the computing device includes instructions to apply a first amperage or voltage to a first variable focal length element of the number of variable focal length elements and a second amperage or voltage to a second variable focal length element of the number of variable focal length elements.

18. The system of claim 17, wherein the first amperage or voltage and the second amperage or voltage are different amperages or voltages.

19. The system of claim 17, wherein the first amperage or voltage and the second amperage or voltage are determined based on the determined distance.

* * * * *